United States Patent
Guerrero-Preston et al.

(10) Patent No.: US 8,728,732 B2
(45) Date of Patent: May 20, 2014

(54) GLOBAL DNA HYPOMETHYLATION AND BIOMARKERS FOR CLINICAL INDICATIONS IN CANCER

(75) Inventors: Rafael Guerrero-Preston, Baltimore, MD (US); David Sidransky, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/408,338

(22) Filed: Feb. 29, 2012

(65) Prior Publication Data

US 2013/0035247 A1 Feb. 7, 2013

Related U.S. Application Data

(60) Provisional application No. 61/448,020, filed on Mar. 1, 2011.

(51) Int. Cl.
*C12Q 1/68* (2006.01)
*C40B 30/04* (2006.01)

(52) U.S. Cl.
USPC .............................................. 435/6.11; 506/7

(58) Field of Classification Search
None
See application file for complete search history.

(56) References Cited

PUBLICATIONS

Harder et al. (2008) "Quantitative promoter methylation analysis of hepatocellular carcinoma, cirrhotic and normal liver" Int. J. Cancer 122(12):2800-2804.*

Guerrero-Preston et al. "B4GALT1 as a potential epigenetic marker of metabolic disruptiopns associated with Non-Alcoholic Fatty Liver Disease" [abstract] In: Proceedings of the American Association for Cancer Research Annual Meeting, vol. 49, Apr. 12-16, 2008; San Diego, CA; p. 907; Abstract #3827.*
Hoque, et al., J. Clin. Oncol., 2005, 23(27):6569-75.
Scacheri, Methods Enzymol., 2006, 411:270-82, Only Abstract is provided; Abstract only considered.
Fang, et al., BMC Bioinformatics, 2008, 9:22.
He, et al., Nucleic Acids Res., 2008, 36(Database issue):D836-41.
Naucler, et al., N. Engl. J. Med., 2007, 357(16):1589-97.

* cited by examiner

*Primary Examiner* — Tracy Vivlemore
*Assistant Examiner* — Karen S Weiler
(74) *Attorney, Agent, or Firm* — Johns Hopkins Technology Transfer (57) ABSTRACT

The present invention provides methods of determination of a global DNA methylation index (GDMI) in a sample from a subject, using a variety of methods which can detect global, genome-wide, and gene-specific DNA methylation to create methylation portraits that can be used for early detection, diagnosis, and clinical management in the personalized medicine space. Further, the invention provides methods of diagnosis of cancer, including gastric cancer and hepatocellular cancer in a subject, by comparing the GDMI in a sample obtained from a subject to the methylation index of standard controls. These methods allow diagnosis of gastric carcinoma and liver cancer in patients who may be asymptomatic or have inconclusive pathology, and allowing earlier treatment of the subject.

2 Claims, 9 Drawing Sheets

| Gene | Forward 5'-3' | Reverse 5"–3" | Genbank # | Annealing Temperature |
|---|---|---|---|---|
| ACTB | TGG TGA TGG AGG AGG TTT AGT AAG T (SEQ ID NO: 1) | AAC CAA TAA AAC CTA CTC CTC CCT TAA (SEQ ID NO: 2) | Y00474 | 60 |
| RASSF1A | GCGTTGAAGTCGGGGGTTC (SEQ ID NO: 3) | CCCGTACTTCGCTAACTTTAAACG (SEQ ID NO: 4) | NM_007182 | 60 |
| B4GALT1 | TAGGAAACGGGTTTCGACG (SEQ ID NO: 5) | CCGTCCACTTCTTTACCG (SEQ ID NO: 6) | NM_001497 | 58 |
| SSBP2 | ATTTTTGCGGTCGTAGCGGT (SEQ ID NO: 7) | TTCTACGACAAATCTAACGAA (SEQ ID NO: 8) | NM_012446 | 60 |
| | Probe 6FAM 5'-3'TAMRA | Amplicon size(Nucleotide range) | | |
| ACTB | ACC ACC ACC CAA CAC ACA ATA ACA AAC ACA (SEQ ID NO: 9) | 133 bp; (390–522) | | |
| RASSF1A | ACAAACGCGAACCGAACGAAACCA (SEQ ID NO: 10) | 75 bp; (45-119) | | |
| B4GALT1 | CGTTAAACAACGAAATCCAACCGAA (SEQ ID NO: 11) | 116 bp; 583-688) | | |
| SSBP2 | ATATCCAAAACGCCGCGAAACTCC (SEQ ID NO: 12) | 89bp; (694-784) | | |

FIGURE 5A

*Hepatocellular carcinoma risk factors per participant*

| Sample ID | Age (y) | Sex | Race | Etiology |
|---|---|---|---|---|
| 1 | 35 | M | W | Other |
| 2 | 4 | M | B | HCV |
| 3 | 9 | F | W | Cryptogenic |
| 4 | 12 | M | W | Cryptogenic |
| 5 | 14 | F | B | Cryptogenic |
| 6 | 15 | M | W | Cryptogenic |
| 7 | 19 | M | W | Cryptogenic |
| 8 | 20 | F | B | HCV |
| 9 | 20 | M | W | HCV |
| 10 | 26 | M | W | HCV |
| 11 | 28 | F | B | Other |
| 12 | 40 | F | B | Cryptogenic |
| 13 | 40 | M | W | Cryptogenic |
| 14 | 40 | M | B | HCV and ETOH |
| 15 | 42 | M | W | ETOH |
| 16 | 45 | M | W | HCV |
| 17 | 45 | M | W | HVB/HCV |
| 18 | 45 | F | W | Cryptogenic |
| 19 | 47 | F | B | HCV |
| 20 | 50 | M | W | HCV |
| 21 | 51 | F | B | HCV |
| 22 | 53 | M | W | Cryptogenic |
| 23 | 54 | F | AS | HBV |
| 24 | 54 | M | W | Other |
| 25 | 55 | M | W | Cryptogenic |
| 26 | 57 | M | W | HCV |
| 27 | 58 | F | B | Other |
| 28 | 58 | M | W | HCV |
| 29 | 58 | M | W | Other |
| 30 | 59 | M | W | HCV |

FIGURE 5B

*Hepatocellular carcinoma risk factors per participant*

| Sample ID | Age (y) | Sex | Race | Etiology |
|---|---|---|---|---|
| 31 | 60 | F | W | Other |
| 32 | 60 | F | W | Other |
| 33 | 61 | M | W | Other |
| 34 | 62 | F | W | Other |
| 35 | 65 | F | W | Other |
| 36 | 67 | M | W | Cryptogenic |
| 37 | 67 | M | W | HCV |
| 38 | 70 | F | B | HCV |
| 39 | 70 | M | W | Other |
| 40 | 73 | M | W | Other |
| 41 | 73 | F | W | Other |
| 42 | 74 | F | W | Other |
| 43 | 81 | F | W | Other |

GLOBAL DNA HYPOMETHYLATION AND BIOMARKERS FOR CLINICAL INDICATIONS IN CANCER

REFERENCE TO RELATED APPLICATIONS

This application claims the benefit of U.S. Provisional Patent Application No. 61/448,020, filed on Mar. 1, 2011, which is hereby incorporated by reference for all purposes as if fully set forth herein.

STATEMENT OF GOVERNMENTAL INTEREST

This invention was made with government support under grant no. CA084986 awarded by the National Cancer Institute and DE019032 awarded by the National Institutes of Health. The government has certain rights in the invention.

BACKGROUND OF THE INVENTION

Epigenomics refers to the inheritance of information based on gene expression levels that do not entail changes in DNA sequence, as opposed to genetics which refers to information transmitted on the basis of gene sequence. The best understood epigenomic marks include DNA methylation, histone modifications, and micro-RNA (miRNA). Epigenomics has been called the science of change. It is a biological endpoint for endogenous and exogenous factors that determine health and disease.

DNA methylation is one of the most common alterations in human neoplasia, including breast cancer. DNA methylation refers to the addition of a methyl group to the cytosine ring of those cytosines that precede guanosine (CpG dinucleosides) to form methyl cytosine. Detection of changes in DNA methylation may offer an alternative to screening and may offer data for long-term management of women treated for breast cancer.

Hepatocellular carcinoma (HCC) is the most common primary malignancy of the liver in adults, the fifth most common solid tumor, and the third most common cause of cancer death worldwide. HCC incidence and death rates are steadily rising in the United States and demonstrate the highest average annual percent increase of the top 15 cancers by incidence. HCC patients, and people at risk of developing HCC, have a profound unmet medical and public health needs. Advances in HCC treatment such as, liver transplantation, surgical resection, and loco regional therapies have only impacted a fraction of the population at risk. More than 70% of HCC patients present with advanced disease and will not benefit from these treatment modalities, or from the sole chemotherapeutic agent approved for advanced HCC patients.

Most HCC patients cannot benefit from current treatment modalities because they are diagnosed with advance disease. The obesity epidemic and the increase in HCV related cirrhosis will eventually lead to an increase in the incidence of HCC. The projected increase in HCC incidence creates an urgent need for translational research that leads to novel screening and clinical management for HCC. HCC mortality, however, can be decreased by effective early detection strategies followed by curative treatment such as resection, liver transplantation, or liver ablation. The smaller the HCC tumor is at diagnosis, the higher the likelihood of therapeutic success. Consequently, the goal of screening programs for at risk populations is to detect and treat HCC at an early stage and, specifically, when tumors can be detected before they have grown larger than 2 cm in diameter.

According to American Association for the Study of Liver Diseases (AASLD) guidelines, HCC screening should be done with ultrasound every 6-12 months. HCC diagnosis requires a specific algorithm with dynamic imaging techniques for the characterization of liver nodules detected during surveillance of patients with cirrhosis with ultrasound (US). A combination of dynamic contrast imaging techniques, contrast-enhanced ultrasound (CE-US), computed tomography (CT), and gadolinium magnetic resonance imaging (MRI), are considered the standard of care for the radiological diagnosis of HCC in cirrhotic patients. However, the accuracy of radiological diagnosis depends largely on the degree of arterial hypervascularization, which increases with tumor size, and also by cell grading of the nodule. HCC diagnostic accuracy could be improved if a molecular biomarker was identified that could distinguish HCC from non-HCC cells in the nodule.

Similar to HCC, gastric cancer (GC) is the fourth most common cancer in both sexes and the second cause of cancer-related death around the world. The prognosis of GC is closely related to the stage of disease at the time of diagnosis. Early GC is defined as cancer confined to the mucosa or submucosa regardless of the presence of lymph node metastasis. Apart from conventional, magnifying narrow-band imaging (NBI), endoscopy has been recently introduced for the diagnosis of early GC. However, missed diagnoses of GC on endoscopy are still common, with false-negative rates ranging from 5 to 19%. Whereas the five year survival rate for early GC is greater than 90%, prognosis for advanced GC is still poor. A contributing factor to this poor prognostication rate is the difficulty in distinguishing early GC from benign peptic ulcer or gastritis in the ambulatory setting, as most of the patients with early GC do not have specific symptoms. Due to the above mentioned reasons, less than 20% of GCs are diagnosed at an early stage in several countries.

The integration of epigenomics and DNA methylation to clinical and population based studies is still lacking. As such, there still exists a need for better clinical methods for determining biomarkers useful in detection and diagnosis of hepatic and gastric cancers.

SUMMARY OF THE INVENTION

In an embodiment, the present invention provides a method for obtaining a global DNA methylation index (GDMI) in a sample comprising a) obtaining a biological sample comprising DNA from a subject, b) determining the amount of 2'-deoxycytidine (2dc) and 5-methyl-2'-deoxycytidine (5mdc) in the DNA sample, c) generating a GDMI for the sample by comparing the amount of 5mdc relative to the amount of 5mdc+2dc in the sample and generating a ratio.

In another embodiment, the present invention provides a method for identifying whether a subject has an increased risk of HCC comprising a) obtaining a biological sample of hepatocytes comprising DNA from a subject, b) determining the amount of 2'-deoxycytidine (2dc) and 5-methyl-2'-deoxycytidine (5mdc) in the DNA sample, c) generating a GDMI for the sample by comparing the amount of 5mdc relative to the amount of 5mdc+2dc in the sample and generating a ratio and d) comparing the GDMI of the sample to the GDMI of a control, wherein when the GDMI of the sample is less than the GDMI of the control, then the subject has an increased risk of HCC.

In a further embodiment, the present invention provides a method of diagnosis of HCC in a subject suspected of having HCC comprising a) obtaining a biological sample of hepatocytes comprising DNA from the subject, b) detecting the amount of promoter methylation on at least one or more DNA target sites selected from the group consisting of RASSF1A, SSBP2, and B4GALT1, and c) comparing the amount of promoter methylation on at least one or more DNA target sites in the sample of the subject to the amount of promoter methylation in a control sample, wherein when the amount of promoter methylation on at least one or more DNA target sites is greater than the amount of promoter methylation in the control sample, the patient is diagnosed as having HCC.

In yet another embodiment, the present invention provides a method for identifying whether a subject has an increased risk of GC comprising a) obtaining a biological sample of the gastric mucosa comprising DNA from a subject, b) determining the amount of 2'-deoxycytidine (2dc) and 5-methyl-2'-deoxycytidine (5mdc) in the DNA sample, c) generating a GDMI for the sample by comparing the amount of 5mdc relative to the amount of 5mdc+2dc in the sample and generating a ratio, and d) comparing the GDMI of the sample to the GDMI of a control, wherein when the GDMI of the sample is less than the GDMI of the control, then the subject has an increased risk of GC.

In still a further embodiment, the present invention provides a method for differentiating whether a subject has a high risk of developing GC or a low risk of developing GC in a subject who is diagnosed with deep gastric inflammation comprising a) obtaining a biological sample of gastric tissue comprising DNA from a subject, b) determining the amount of 2'-deoxycytidine (2dc) and 5-methyl-2'-deoxycytidine (5mdc) in the DNA sample, c) generating a GDMI for the sample by comparing the amount of 5mdc relative to the amount of 5mdc+2dc in the sample and generating a ratio and d) comparing the GDMI of the sample to the GDMI of a control, wherein when the GDMI of the sample is less than the GDMI of the control, then the subject has a high risk of GC.

BRIEF DESCRIPTION OF THE DRAWINGS

FIG. 7 shows quantitative methylation specific PCR (QMSP) results of Hepatocellular carcinoma samples and adjacent normal liver samples that were bisulfate treated to examine the promoter methylation status of RASF1A, B4GALT1 and SSBP2. Scatter plots of QMSP analysis of candidate gene promoters. Eighteen adjacent normal liver tissue samples and 27 hepatocellular carcinoma samples were tested for methylation for each of the three genes by quantitative MSP. The relative level of methylated DNA for each gene in each sample was determined as a ratio of MSP for the amplified gene to ACTB and then multiplied by 100 for easier tabulation (average value of duplicates of gene of interest/ average value of duplicates of ACTB)×100. The samples were categorized as unmethylated or methylated based on detection of methylation above a threshold set for each gene. This threshold was determined by analyzing the levels and distribution of methylation, if any, in normal, age-matched tissues.

FIG. 8 depicts ROC curves for a panel of the three genes RASSF1A, B4GALT1 and SSBP2 by themselves (8A) and after adjusting a logistic regression model with HCC risk factors: age, gender, ethnicity and etiology. (8B)

DETAILED DESCRIPTION OF THE INVENTION

One of the aims of the present invention was to develop a Phase I biomarker using the GDMI, and determine whether it could distinguish HCC and GC cases from controls in two ambulatory clinics that monitor a great number of high risk patients diagnosed with premalignant or early hepatic and gastric cancer lesions.

In an embodiment, the present invention provides a method for obtaining a GDMI in a sample comprising a) obtaining a biological sample comprising DNA from a subject, b) determining the amount of 2'-deoxycytidine (2dc) and 5-methyl-2'-deoxycytidine (5mdc) in the DNA sample, c) generating a GDMI for the sample by comparing the amount of 5mdc relative to the amount of 5mdc+2dc in the sample and generating a ratio.

In accordance with another embodiment of the present invention, it will be understood that the term "biological sample" or "biological fluid" includes, but is not limited to, any quantity of a substance from a living or formerly living patient or mammal Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

It will be understood by those of ordinary skill, that there are a number of ways to detect DNA methylation, and these are known in the art. Examples of preferred methods of detection of methylation of DNA in a sample include the use of QMSP, oligonucleotide methylation tiling arrays, paramagnetic beads linked to MBD2, i.e., BeadChip assays and HPLC/MS methods. Other methods include methylation-specific multiplex ligation-dependent probe amplification (MS-MPLA), bisulfate sequencing, and assays using antibodies to DNA methylation, i.e., ELISA assays. The methylation state or GDMI information gathered from these methods can be generated using any type of microprocessor or computing device.

As used herein, the term "methylation state" means the detection of one or more methyl groups on a cytidine in a target site of the DNA in the sample.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

It will be understood that the methods of the present invention which determine the methylation state of a sample of DNA (GDMI) are useful in preclinical research activities as well as in clinical research in various diseases or disorders, including, for example, cancer.

In accordance with an embodiment, the present invention provides a method for identifying whether a subject has an increased risk of HCC comprising a) obtaining a biological sample of hepatocytes comprising DNA from a subject, b) determining the amount of 2'-deoxycytidine (2dc) and 5-methyl-2'-deoxycytidine (5mdc) in the DNA sample, c) generating a GDMI for the sample by comparing the amount of 5mdc relative to the amount of 5mdc+2dc in the sample and generating a ratio and d) comparing the GDMI of the sample to the GDMI of a control, wherein when the GDMI of the sample is less than the GDMI of the control, then the subject has an increased risk of HCC.

Conversely, if the GDMI of the sample is the same or greater than the GDMI of the control, then the subject does not have an increased risk of developing HCC.

In accordance with an embodiment, the present invention provides a method of diagnosis of HCC in a subject suspected of having HCC comprising a) obtaining a biological sample of hepatocytes comprising DNA from the subject, b) detecting the amount of promoter methylation on at least one or more DNA target sites selected from the group consisting of RASSF1A, SSBP2, and B4GALT1, and c) comparing the amount of promoter methylation on at least one or more DNA target sites in the sample of the subject to the amount of promoter methylation in a control sample, wherein when the amount of promoter methylation on at least one or more DNA target sites is greater than the amount of promoter methylation in the control sample, the patient is diagnosed as having HCC.

It will be understood by those of ordinary skill, that a diagnosis of HCC can be made by detection of increased methylation of RASSF1A and/or SSBP2 and/or B4GALT1. Examples of subjects suspected of having HCC can include, for example, subjects being chronically infected with Hepatitis B virus, Hepatitis C virus, and subjects suffering from chronic alcoholism.

In yet another embodiment, the present invention provides a method for identifying whether a subject has an increased risk of GC comprising a) obtaining a biological sample of the gastric mucosa comprising DNA from a subject, b) determining the amount of 2'-deoxycytidine (2dc) and 5-methyl-2'-deoxycytidine (5mdc) in the DNA sample, c) generating a global DNA methylation index (GDMI) for the sample by comparing the amount of 5mdc relative to the amount of 5mdc+2dc in the sample and generating a ratio, and d) comparing the GDMI of the sample to the GDMI of a control, wherein when the GDMI of the sample is less than the GDMI of the control, then the subject has an increased risk of GC.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream. The cancer can be any cancer, including any of acute lymphocytic cancer, acute myeloid leukemia, alveolar rhabdomyosarcoma, adenocarcinoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, hepatocellular cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The cancer can be an epithelial cancer. As used herein the term "epithelial cancer" refers to an invasive malignant tumor derived from epithelial tissue that can metastasize to other areas of the body, e.g., a carcinoma. Preferably, the epithelial cancer is breast cancer. Alternatively, the cancer can be a non-epithelial cancer, e.g., a sarcoma, leukemia, myeloma, lymphoma, neuroblastoma, glioma, or a cancer of muscle tissue or of the central nervous system (CNS).

The cancer can be a non-epithelial cancer. As used herein, the term "non-epithelial cancer" refers to an invasive malignant tumor derived from non-epithelial tissue that can metastasize to other areas of the body.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein. Preferably, the cancer is a metastatic cancer.

The phrase "controls or control materials" refers to any standard or reference tissue or material that has not been identified as having cancer. The GDMI is calculated by determining the amount of 2'-deoxycytidine (2dc) and 5-methyl-2'-deoxycytidine (5mdc) in the unknown DNA sample and comparing the amount of 5mdc relative to the amount of 5mdc+2dc in the sample and generating a ratio. This is then compared to the GDMI of a control sample.

The nucleic acids used as primers in embodiments of the present invention can be constructed based on chemical synthesis and/or enzymatic ligation reactions using procedures known in the art. See, for example, Sambrook et al. (eds.), Molecular Cloning, A Laboratory Manual, 3$^{rd}$ Edition, Cold Spring Harbor Laboratory Press, New York (2001) and Ausubel et al., Current Protocols in Molecular Biology, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleotide sequences used herein are those which hybridize under stringent conditions preferably hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C.

As used herein, the term "host cell" refers to any type of cell that can contain the viral DNA disclosed herein. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, BC-3 cells, and the like. In an embodiment, the host cell is preferably a mammalian cell. Most preferably, the host cell is a human cell or human cell line. The host cell can be of any cell type, can originate from any type of tissue, and can be of any developmental stage.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein having structural, regulatory, or biochemical functions of a naturally occurring molecule.

The term "reacting" in the context of the embodiments of the present invention means placing compounds or reactants in proximity to each other, such as in solution, in order for a chemical reaction to occur between the reactants.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, screening, or other patient management, including treatment or prevention of cancer in a mammal Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

EXAMPLES

Gastric tissue samples and DNA extraction. A total of 402 samples were collected at the National Institute de Neoplasicas (NEO) and the National Hospital Arzobispo Loayza (LOY) in Lima, Perú, from 75 gastric cancer patients (case study group) and 126 individuals diagnosed with gastritis (control study group). Two sample biopsies were taken from each patient (201 patients in total for both study groups, mean age of 62.5±15.1 years, age range 18-88 years). Informed written consent was obtained from all patients included in the study and research protocols were approved by Institutional Review Boards of the National Institute de Neoplasicas, the National Hospital Arzobispo Loayza, the Universidad Peruana Cayetano Heredia and the Johns Hopkins University School of Medicine.

The criteria for a patient's inclusion in the study were to either have gastro-duodenal symptoms or a suspicion of gastric cancer. Patients came to the clinic referring symptoms including, for example, heartburn (81.8%), belching (76.4%), distension (74.2%), abdominal pain (51.1%), nausea (39.6%) and acid regurgitation (26.3%). Biopsies were obtained from the cancer lesion and from the gastric antrum for the controls. Tissue was then fixed in 10% formalin buffer and embedded in paraffin for microscopy histological examination. Hematoxylin and eosin-stained histological slides were scored using the Sydney System. Biopsies indicative of intestinal metaplasia or *H. pylori* infection were also stained with PAS. All the neoplastic tissue used in this study was classified as gastric adenocarcinoma, and was confirmed by histopathology.

DNA from the tissue samples was extracted using the QIAmp DNA Mini Kit (QIAGEN, Germany) and stored at −20° C. until use. DNA concentrations were measured using Nanodrop ND-1000 spectrophotometer.

Gastric global methylation analysis. Global DNA methylation levels were determined by ELISA using the MDQ1, Imprint™ Methylated DNA Quantification Kit (Sigma, St. Louis, Mo.) according to manufacturer's instructions. Quantification was based on the estimation of GDMI that was obtained by a single point method. The differential methylation levels of the samples were relative to the methylated control DNA. Each analysis for the blank, sample(s) and control DNA had been performed in duplicate, and the average of the absorbance readings at 450 nm ($A_{450}$) was used for calculations. The global DNA methylation level for each sample was calculated according to the equation:

$$[(A_{450av}\text{Sample} - A_{450av}\text{Blank})/(A_{450av}\text{Methylated Control DNA} - A_{450av}\text{Blank})] \times 100.$$

HCC Patient selection. De-identified frozen primary HCC, adjacent non-tumor (cirrhotic and non-cirrhotic), and normal liver (non-cirrhotic tissue obtained from autopsies) tissue samples were obtained from the Johns Hopkins University School of Medicine and the Human Cooperative Tissue Network. The study protocol conforms to the ethical guidelines of the 1975 Declaration of Helsinki as reflected in a priori approval by the Johns Hopkins Institutional Review Board. All patients had not undergone therapy prior to sample collection. The samples were frozen in liquid nitrogen and stored in −80° C.

HCC DNA extraction, bisulfite conversion and MeDIP enrichment. Tissue samples were digested with 1% SDS and 50 μg/ml proteinase K (Bushranger Mannheim) at 48° C. overnight, followed by phenol/chloroform extraction and ethanol precipitation of DNA as previously described. Prior to using QMSP and the Illumina BeadChip assay bisulfite modification of 2 ug of genomic DNA was performed as previously described (J. Clin. Oncol., 2005, 23(27):6569-75). Prior to using the Nimblegen tiling arrays 500 ng of genomic DNA was sheared using a water bath sonicator (Bioruptor UCD-200, Diagenode). Sonicated DNA was then analyzed on a 1.5% agarose gel to ensure that it had an optimal size of 200-1000 bp. MeDIP was subsequently performed with the Methyl DNA Immunoprecipitation Kit (Epigentek). Fractions of Input DNA and Immunoprecipitated DNA from each sample were subsequently sent to Nimblegen for labeling, hybridization and scanning.

Illumina BeadChip array. Bisufite treated DNA from 3 HCC samples and 3 adjacent normal liver samples was hybridized to the HumanMethylation 27K BeadChip, which quantitatively interrogates 27,578 CpG loci covering more than 14,000 genes at single-nucleotide resolution. The Infinium Methylation assay detects cytosine methylation at CpG islands based on highly multiplexed genotyping of bisulfite-converted genomic DNA (gDNA). The assay interrogates these chemically differentiated loci using two site-specific probes, one designed for the methylated locus (M bead type) and another for the unmethylated locus (U bead type). Single-base extension of the probes incorporates a labeled ddNTP, which is subsequently stained with a fluorescence reagent. The level of methylation for the interrogated locus can be determined by calculating the ratio of the fluorescent signals from the methylated vs. unmethylated sites.

Nimblegen 385K CpG Island Plus Promoter Array. DNA (500 ng) from 3 liver tissue samples (1 HCC and 2 non-cirrhotic normal liver samples) enriched with MeDIP were hybridized to Nimblegen Promoter plus CpG Island 385K oligonucleotide tiling arrays. A single array design covers 28,226 CpG islands and promoter regions for 17,000 RefSeq genes. The promoter region covered is 1 kb long: 800 by upstream from the Transcription Start Site and 200 by downstream from the transcription start site. Small CpG islands are extended at both ends for a total additional coverage of 700 by for more reliable detection. DNA methylation positive control regions, such as the HoxA gene cluster, H19/IGF2 cluster, KCNQ1 cluster, and IGF2R gene, are also included on the array.

Bioinformatics analysis of methylation array data. The Microarray Core at Johns Hopkins School of Medicine performed the bioinformatics analysis of the Infinium array data using Illumina's proprietary BeadStudio™ software package to provide average methylation Beta values for each probe. Nimblegen performed the bioinformatics analysis for the 385K CpG Island Plus Promoter Array. Nimblegen uses the ACME algorithm to identify hypermethylated genes that have a statistically significant methylation peak score above 2 (Methods Enzymol., 2006, 411:270-82).

Gene selection from public databases of known methylation events in cancer. Candidate gene selection for promoter methylation analysis was performed utilizing existing databases of known methylation events in cancer (BMC Bioinformatics, 2008, 9:22; Nucleic Acids Res., 2008, 36(Database issue):D836-41). We generated a list of genes that have been previously shown to be hypermethylated in HCC and in other tumor tissues. We ranked the list by the frequency in which the genes had been identified in different studies. From this list we choose three genes to develop QMSP primers and probes that examine an 800 by region upstream from the transcription start site using the following inclusion criteria. One of the genes, sequence-specific single-stranded DNA-binding protein 2 (SSBP2) was shown to be hypermethylated in other solid tumors. A second gene, beta-1,4-galactosyl-transferase-1 (B4GALT1), has not been previously shown to be hypermethylated in cancer. The third gene, Ras association domain family member 1 (RASSF1A), was shown to be hypermethylated in HCC.

Quantitative Methylation Specific PCR. DNA from 27 HCC and 21 adjacent normal tissue samples (cirrhotic, non-cirrhotic and cryptogenic) was bisulfate treated and analyzed with QMSP. Fluorogenic PCR reactions were carried out in a reaction volume of 20 μL consisting of 600 nmol/l of each primer; 200 μmol/l probe; 0.75 units platinum Taq polymerase (Invitrogen); 200 μmol/l of each dATP, dCTP, dGTP, and dTTP; 200 nmol/l ROX dye reference (Invitrogen); 16.6 mmol/l ammonium sulfate; 67 mmol/l Trizma (Sigma, St. Louis, Mo.); 6.7 mmol/l magnesium chloride; 10 mmol/l mercaptoethanol; and 0.1% DMSO. Duplicates of three microliters (3 μl) of bisulfite-modified DNA solution were used in each real-time methylation-specific PCR (QMSP) amplification reaction. Primers and probes were designed to specifically amplify the promoters of the three genes of interest (RASSF1A, SSBP2 and B4GALT1) and the promoter of a reference gene, actin-B (ACTB). Primer and probe sequences and annealing temperatures are provided in FIG. 4.

Amplification reactions were carried out in 384-well plates in a 7900HT Fast Real-Time PCR System (Applied Biosystems) and were analyzed by SDS 2.2.1 Sequence Detector System (Applied Biosystems). Thermal cycling was initiated with a first denaturation step at 95° C. for 3 minutes, followed by 40 cycles of 95° C. for 15 seconds and 58° C. for 1 minute. Each plate included patient DNA samples, positive (Bisulfate-converted Universal Methylated Human DNA Standard (Zymo Research)) and negative (normal leukocyte DNA or DNA from a known unmethylated cell line) controls, and multiple water blanks. Serial dilutions (60 ng, 6 ng, 0.6 ng, 0.06 ng and 0.006 ng) of Bisulfite-converted Universal Methylated Human DNA Standard (ZYMO RESEARCH™) were used to construct a standard curve for each gene.

Statistical analysis for QMSP and methylation array data. QMSP values were adjusted for DNA input by expressing results as ratios between 2 absolute measurements. The relative level of methylated DNA for each gene in each sample was determined as a ratio of QMSP for the amplified gene to ACTB and then multiplied by 100 for easier tabulation ((average DNA quantity of methylated gene of interest/average DNA quantity for internal reference gene b-actin)×100). The samples were categorized as unmethylated or methylated based on detection of methylation above a threshold set for each gene. For quality control, all amplification curves were visualized and scored without knowledge of the clinical data. ROC curves were used to identify a cut-off ratio above the highest control ratio observed for each gene to set specificity at 100%. Hypermethylation ratios for each gene were compared between cancer HCC and non-HCC samples. Once the best individually discriminating genes were found, 2-gene, 3-gene panels were tested to identify the highest sensitivity with specificity set at 100% for each gene.

Statistical analysis. All data were calculated using the commercially available software package, STATA/IC 10 (Statacorp, Tex., USA) and results with a p<0.05 were considered as statistically significant. Student's t-test or ANOVA test was used for analyzing distributions or variances respectively.

Example 1

Patients' characteristics and design of the GC case control study. Between March 2004 and June 2010, a total of 201 patients met the eligible criteria and were included in our study. Utilizing the updated Sydney system for the classification of gastritis, 25 cases clinically diagnosed as cancer, were characterized as gastritis by pathologists at two separate institutions. Thus a second study cohort had been introduced, consisted of 50 patients in the case study group and 151 patients in the control study group. Table 1 summarizes the pathological characteristics of the patients comprising the control study group.

TABLE 1

Classification of control study group (gastritis patients) according to pathological characteristics.

| Histology | Controls | |
|---|---|---|
| | Superficial Inflammation | Depth Inflammation |
| Level of inflammation | | |
| Mild | 41 | 18 |
| Moderate | 33 | 34 |
| Severe | 12 | 12 |
| n/d[a] | | 1 |
| Atrophy | | |
| Negative | 85 | 40 |
| Positve | 2 | 24 |
| Intestinal Metaplasia | | |
| Negative | 83 | 34 |
| Positive | 4 | 30 |
| Helicobacter Pylori | | |
| Negative | 33 | 36 |
| Positive | 54 | 27 |
| n/d[a] | | 1 |

[a]No available data

Example 2

Evaluation of GDMI and statistical analysis and discrimination between control and case study group.

Figure 1:
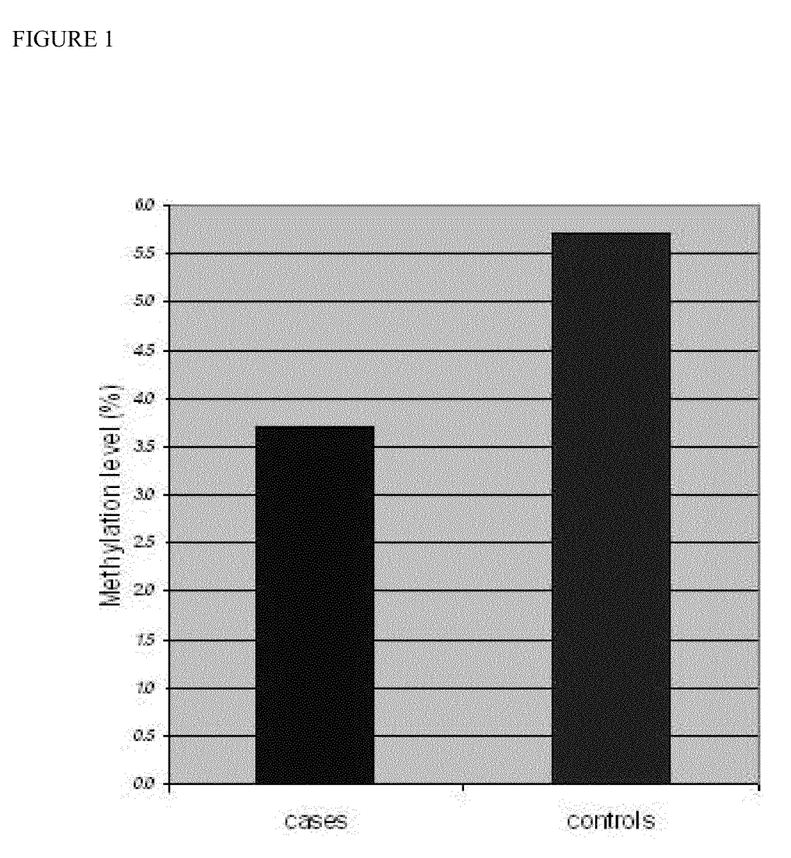
FIG. 1 is a histogram depicting the GDMI in cases and controls study groups.

The control cases found to possess an increased prevalence of global DNA methylation whereas the case study group had a global hypomethylation profile. The mean GDMI for the control study group was estimated to 5.7 (95% CI, 4.93-6.41) and the mean GDMI for the case study group was 3.7 (95% CI, 2.99-4.39), providing a statistical significant discrimination between the two groups (p=0.0016) (FIG. 1).

Example 3

Evaluation of GDMI according to histological classification in control study group.

The statistical analysis of the control study group was separated into two parts, according to the grade of inflammation. First DNA methylation levels were measured among all gastritis patients to distinguish those with superficial inflammation, and deep inflammation. Subsequently, the patients with deep inflammation were discriminated by pathological characteristics.

Figure 2:
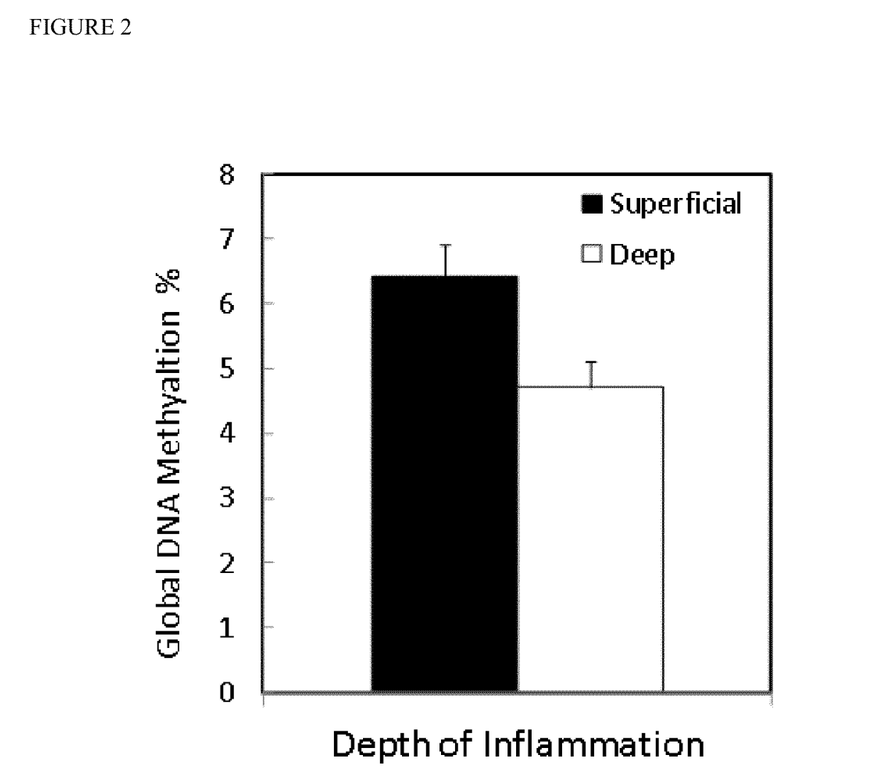
FIG. 2 is a histogram depicting GDMI in gastritis patients with superficial inflammation and deep inflammation.

Among all gastritis patients, a statistically significant difference (p=0.02) was found in the GDMI between patients with superficial (mean GDMI=6.4, 95% CI, 5.34-7.5) and deep inflammation (mean GDMI=4.7, 95% CI, 3.74-5.56). Samples from gastritis patients with superficial inflammation were found to be more frequently methylated when compared to samples from gastritis patients with deep inflammation (FIG. 2).

Example 4

Figure 3:
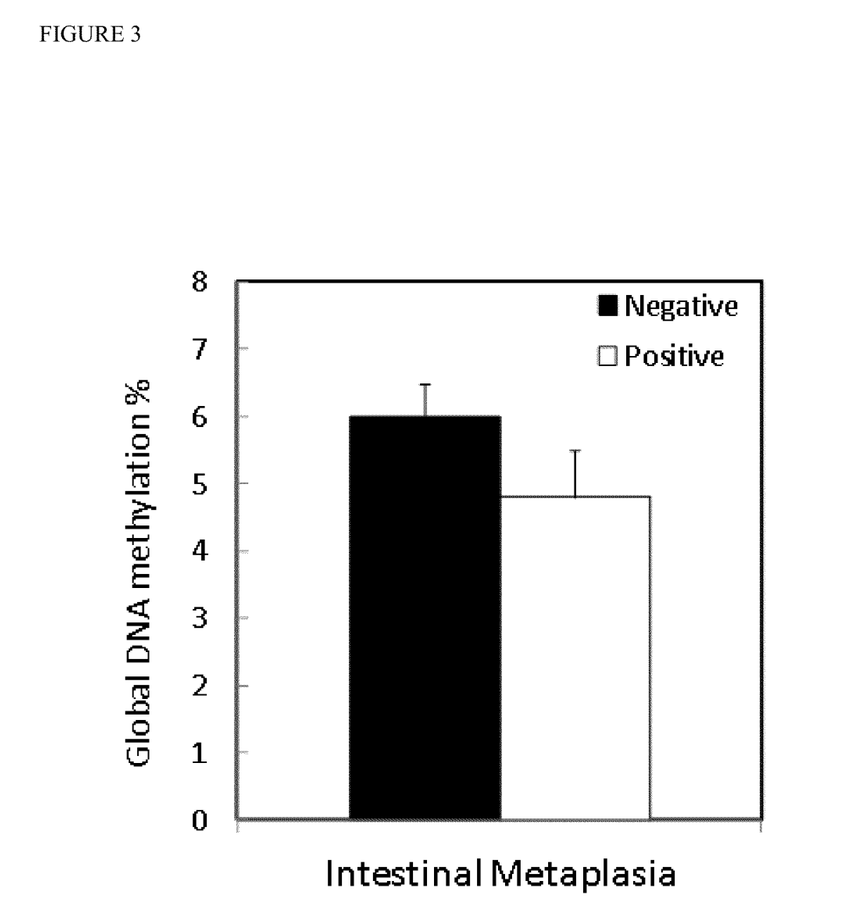
FIG. 3 is a histogram showing GDMI in gastritis patients with deep inflammation who are positive and negative for intestinal metaplasia, a premalignant lesion which may lead to GC.

Among the gastritis patients with deep inflammation, a significant difference was found in the GDMI when comparing samples that were negative and positive for intestinal metaplasia, with the later presenting lower global methylation levels (p=0.03, mean GDMI=5.5, 95% CI, 3.98-6.93 in negative cases and mean GDMI=3.7, 95% CI, 2.75-4.73 in positive ones) (FIG. 3).

Example 5

Figure 5A:
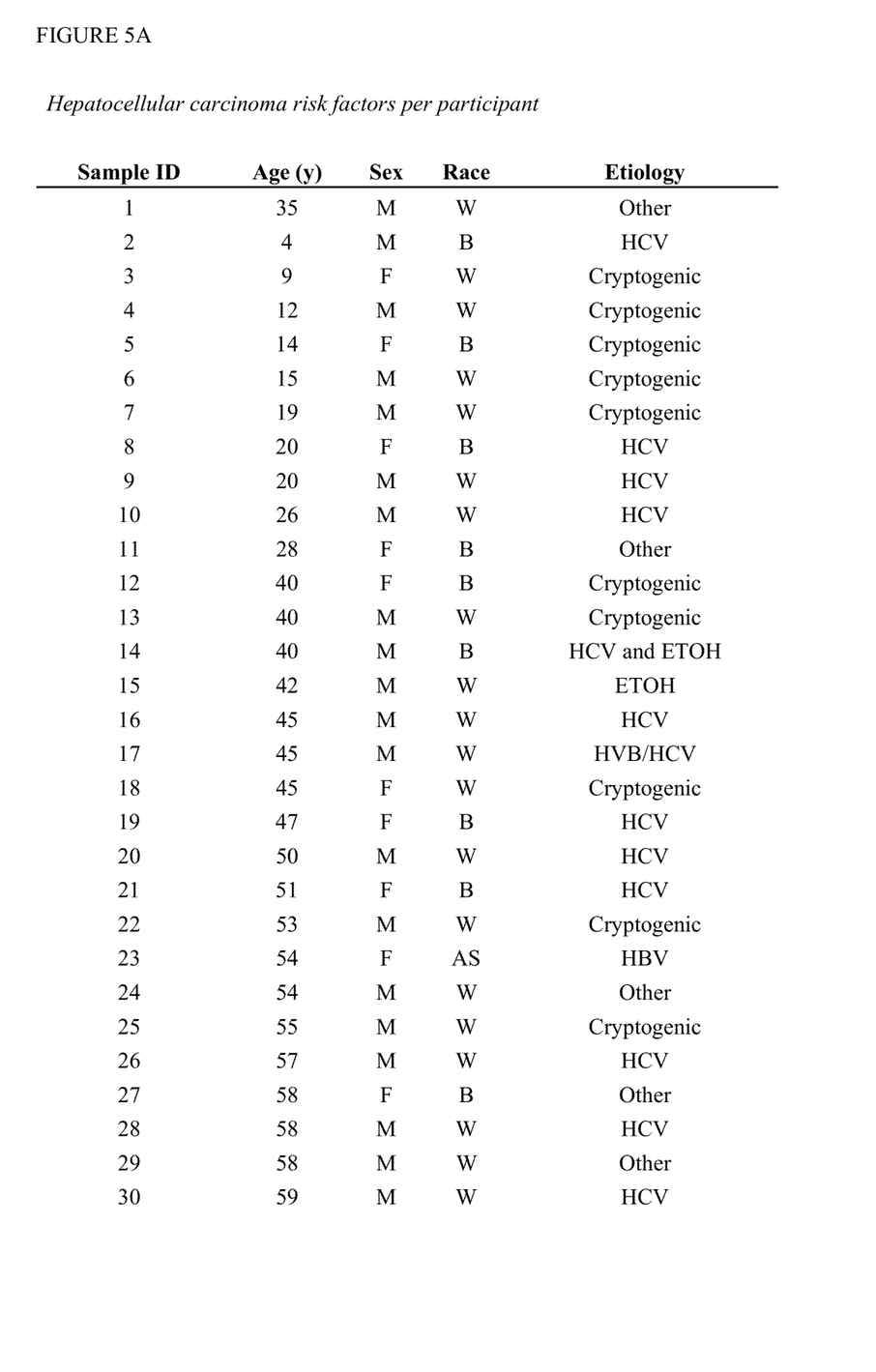
FIG. 5 is a table showing the patient data for the HCC studies.
Figure 5B:
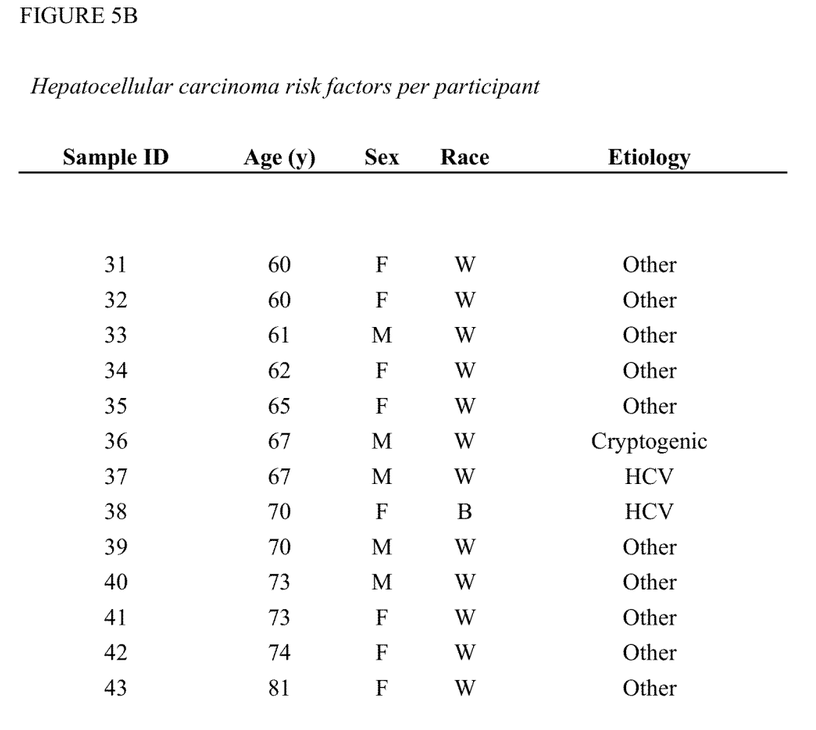

Patient characteristics of the liver cancer case control study can be seen in FIG. 5. The majority (58%) of the patients in our study were men. The mean age of the patients in this study was 47.3 years, and most of (56%) of patients were over 50 years old. The ethnicity of the patients in our study was White (74%), Black (23%) and Asian (2%). The most frequent HCC risk factor seen in the patients of this study was viral infection with HCV (35%) or HBV (5%). Interestingly cryptogenic cirrhosis was seen in 26% of the patients. Alcohol intake was the risk factor for a handful of patients (5%).

Example 6

Figure 6:
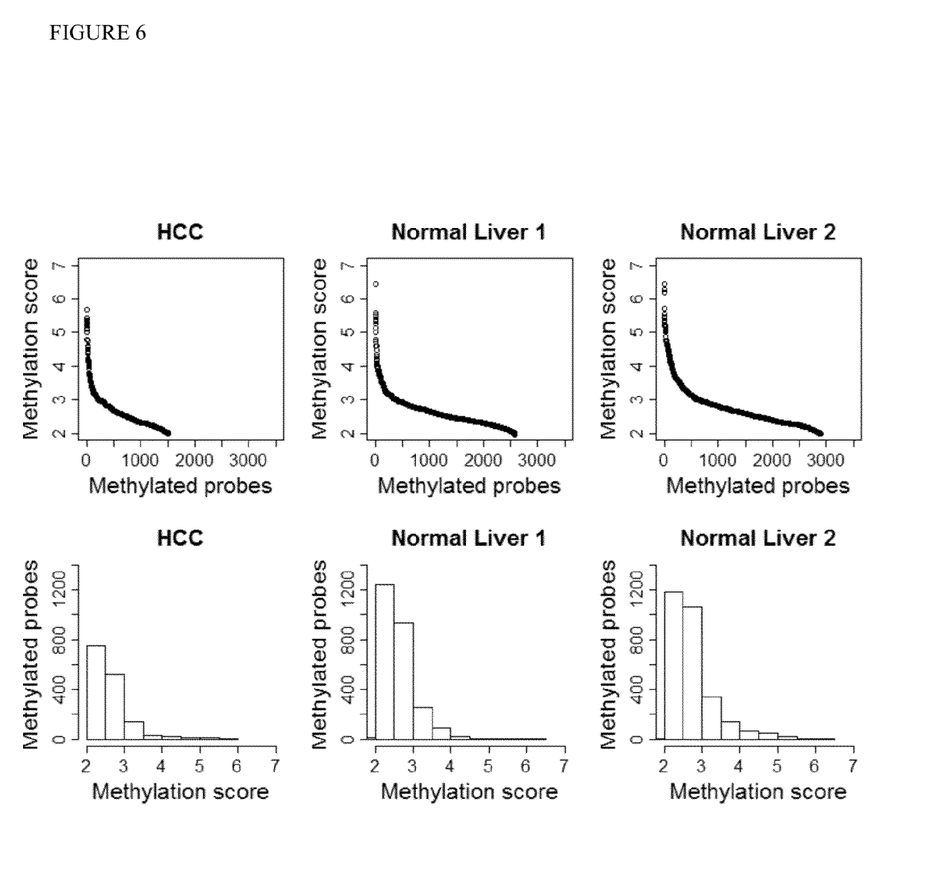
FIG. 6 comprises scatterplots and histograms for a representative set of one tumor sample and two normal samples hybridized to oligonucelotide methylation tiling arrays. The methylation score is on the Y axis of the scatterplots and the number of methylated probes is on the X axis. The number of methylated probes is on the Y axis of the histograms and the methylation score is on the X axis.

Global and gene specific differential DNA promoter methylation arrays. Scatterplots were used to compare global and gene specific promoter DNA methylation values between HCC normal liver tissue samples hybridized to the 385K Nimblegen tiling array after DNA enrichment with MeDIP (MeDIP-chip). FIG. 6 shows representative scatterplots and histograms in which a decrease in global DNA promoter methylation clearly distinguishes between HCC and normal tissue. Scatterplots and histograms of promoter-wide DNA methylation array data provide a snapshot of the differences in methylation patterns between tumor and normal samples. Promoter-wide promoter hypomethylation was observed in the tumor when compared to normal samples. The representative tumor sample has less significant methylated probes (1,503) than either one of the normal liver tissue samples (2,585 and 2,2887 respectively). Furthermore, the median methylation score was significantly lower for the tumor sample (5.7) than for the normal samples (6.7).

Unsupervised clustering was used to create heat maps, comparing gene specific methylation between HCC samples and adjacent normal liver samples (data not shown).

Example 7

Figure 4:
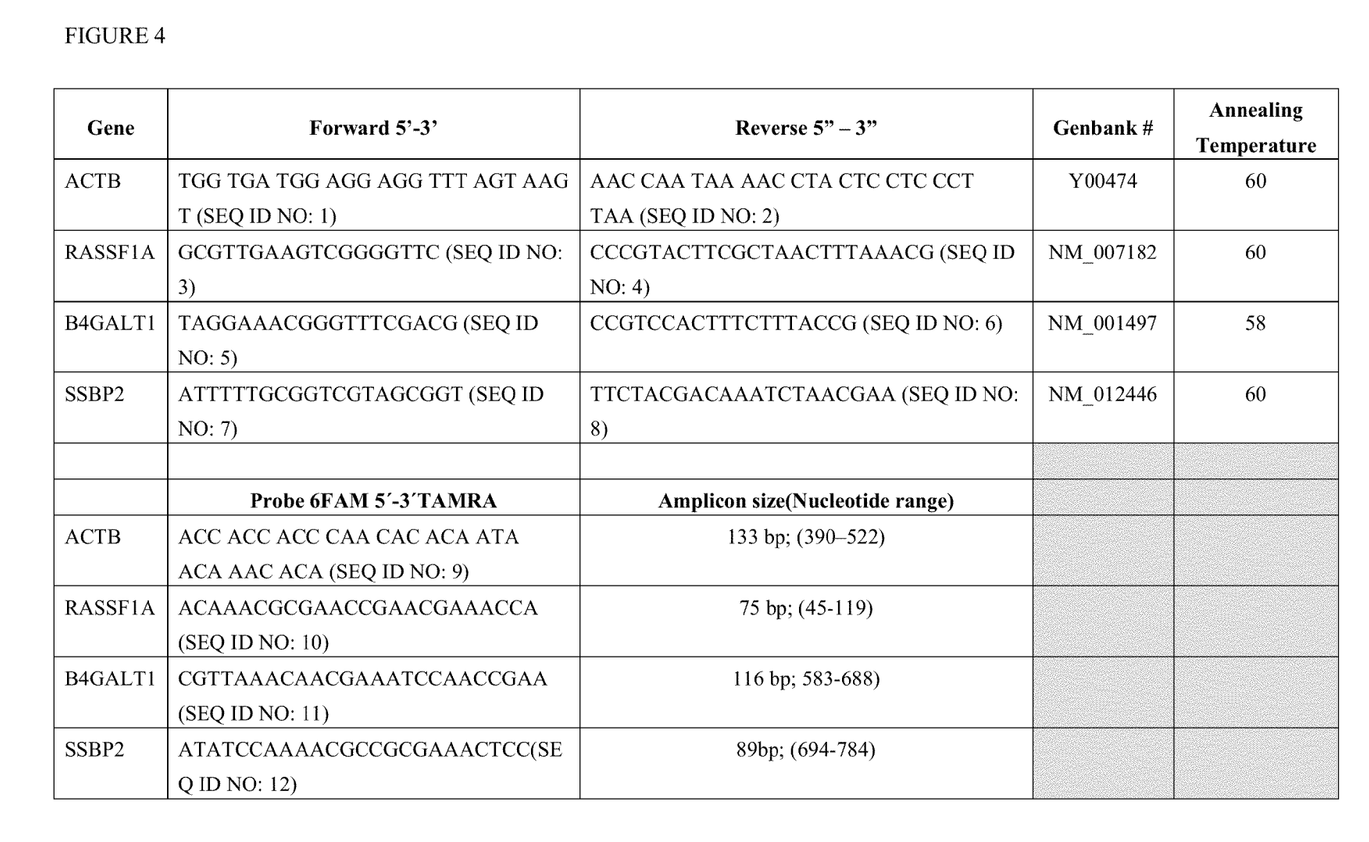
FIG. 4 is a table listing the QMSP Primers and probes used in the present invention.

Promoter hypermethylation in tumor and adjacent normal samples. A search of publicly available methylation databases found a combined total of 549 methylated genes when searching for hepatocellular carcinoma (389) and hepatoma (160), 451 of which were unique genes. Promoter methylation of 3 genes was then quantified. One gene was already found to be hypermethylated in HCC by several groups (RASSF1A), and two genes that were found to be methylated in other tumors but not in HCC (B4GALT1 and SSBP2). The promoter methylation of these 3 genes were quantified in 27 HCC samples and 20 adjacent normal samples. To determine the frequency of methylation primers and probes were used for QMSP previously designed in our laboratory based on bisulfate sequencing data. FIG. 4 provides the primer and probe sequences for these three genes. Area under the curve was calculated using known methods (N. Engl. J. Med., 2007, 357(16):1589-97).

Example 8

Figure 7:
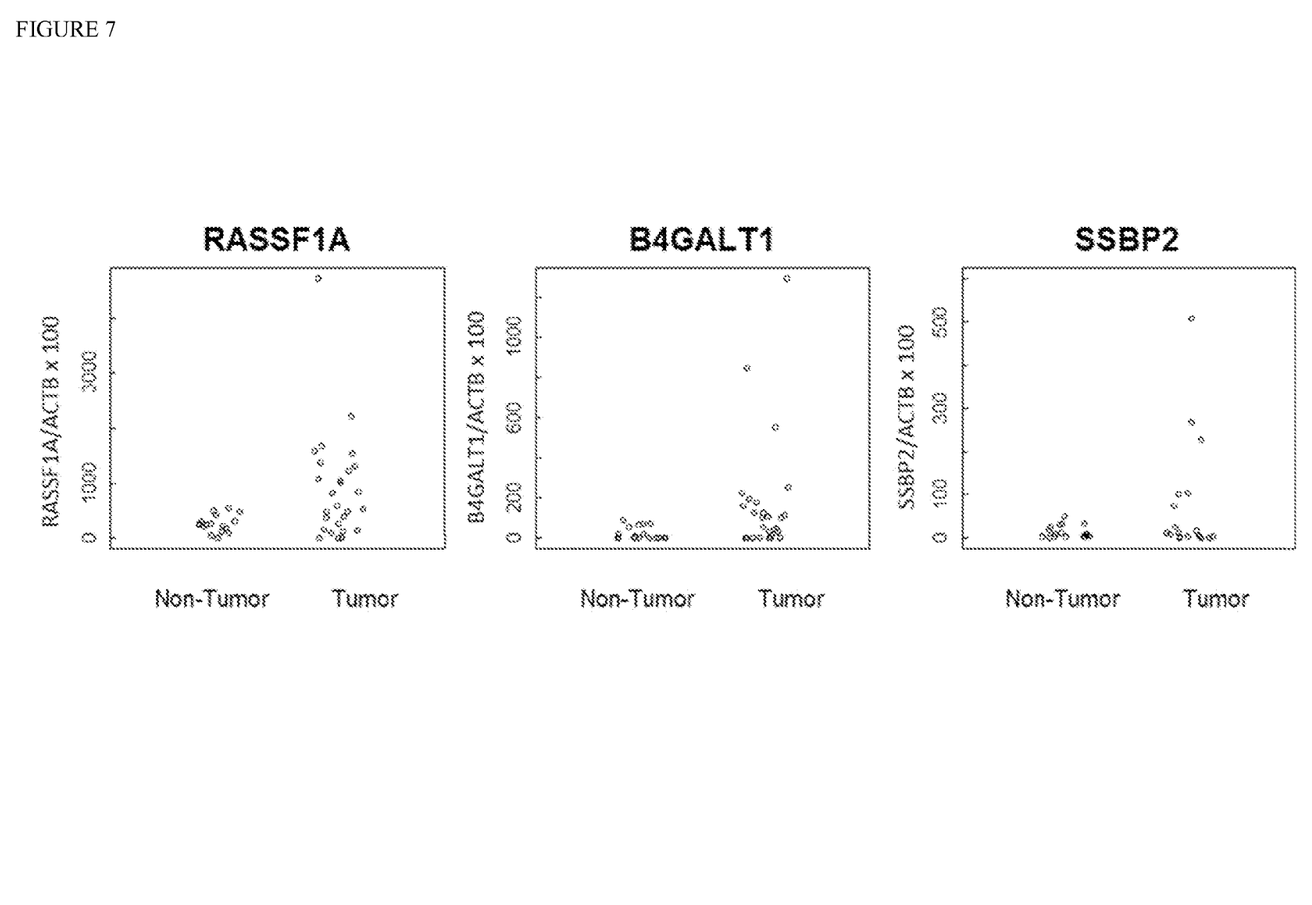

RASSF1A was methylated in 14/27 (52%) of HCC samples and in 1/17 (6%) of adjacent normal samples. B4GALT1 was methylated in 14/27 (52%) of HCC samples and in 0/20 (0%) of adjacent normal samples. SSBP2 was methylated in 14/27 (52%) of HCC samples and in 6/18 (33%) of adjacent normal samples. Most of the HCC samples (78%) had at least one of these three genes methylated, while less than half of the adjacent normal samples (44%) had one gene methylated. Methylation of at least two of these genes was observed in 70% of the HCC samples and in 0% of the adjacent normal samples (FIG. 7).

Example 9

Figure 8A:
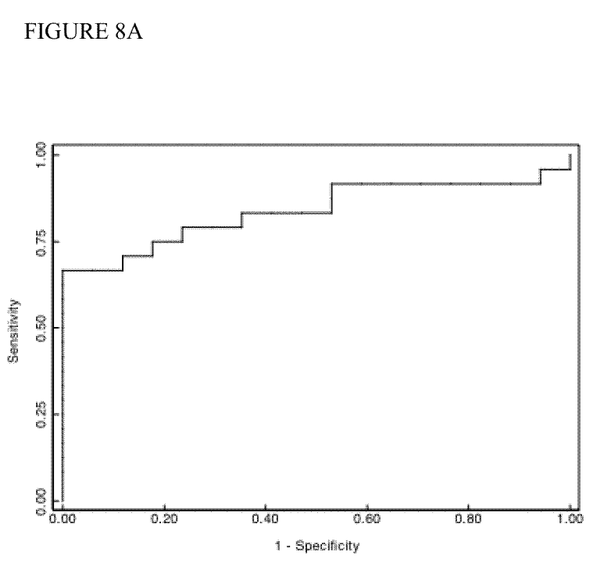

ROC curves were used to determine the sensitivity and specificity of the three genes individually and combined in a biomarker panel (FIG. 8A) RASSF1A methylation in the examined tissue samples had a sensitivity of 52%, a specificity of 100% and an AUC of 0.73 (95% CI, 0.57-0.88). B4GALT1 methylation in the examined tissue samples had a sensitivity of 52%, a specificity of 100% and an AUC of 0.75 (95% CI, 0.71-0.89). SSBP2 methylation in the examined tissue samples had a sensitivity of 38%, a specificity of 100% and an AUC of 0.58 (95% CI, 0.40-0.75) (Table 2).

Figure 8B:
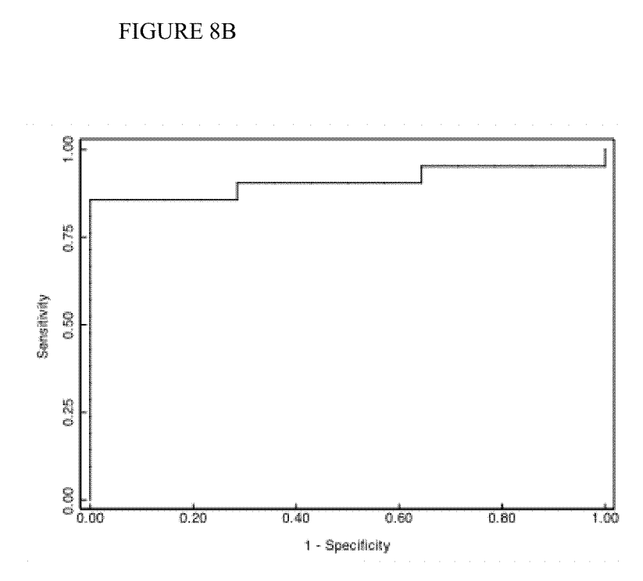

When the methylation status of these three genes was included in a logistic regression model together with gender, age and etiology the sensitivity was 87%, the specificity was 100% and the AUC was 0.91 (FIG. 8B)

The methods of the present invention provide promoter-wide and gene-specific methylation platforms that interrogate the promoter region can be used to distinguish between HCC and non-HCC tissue.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for identifying a subject as having hepatocellular carcinoma (HCC) comprising:
   a) obtaining a biological sample of hepatocytes comprising DNA from the subject;
   b) performing bisulfite modification to the DNA in a);
   c) performing quantitative real-time methylation specific PCR (QMSP) on bisulfite modified DNA from the sample using PCR primers and probes specific for the promoter region of the genes of interest, wherein the genes of interest consist of RASSF1A, SSBP2, and B4GALT1;
   d) determining the promoter methylation level of the promoter regions of the genes of interest in the DNA from the hepatocyte tissue sample of the subject;
   e) providing a reference non-neoplastic hepatocyte tissue sample;
   f) comparing the level of methylation of the promoter region of the genes of interest from the hepatocyte tissue sample of the subject, to the level of methylation of the promoter region of the genes of interest in a reference non-neoplastic-hepatocyte tissue sample; and
   g) identifying said human subject as having HCC when the level of methylation of the promoter region of the genes of interest in the hepatocyte tissue sample of the subject, is greater than the level of methylation of the promoter region of the genes of interest in a reference non-neoplastic hepatocyte tissue sample.

2. The method of claim 1, wherein the subject is infected with Hepatitis B virus (HBV) or Hepatitis C virus (HCV).

* * * * *

SEQUENCE LISTING

```
<160> NUMBER OF SEQ ID NOS: 12

<210> SEQ ID NO 1
<211> LENGTH: 25
<212> TYPE: DNA
<213> ORGANISM: Homo sapiens

<400> SEQUENCE: 1
tggtgatgga ggaggtttag taagt                                          25

<210> SEQ ID NO 2
<211> LENGTH: 27
<212> TYPE: DNA
<213> ORGANISM: Homo sapiens
```

```
<400> SEQUENCE: 2
aaccaataaa acctactcct cccttaa                                27

<210> SEQ ID NO 3
<211> LENGTH: 18
<212> TYPE: DNA
<213> ORGANISM: Homo sapiens

<400> SEQUENCE: 3
gcgttgaagt cggggttc                                          18

<210> SEQ ID NO 4
<211> LENGTH: 24
<212> TYPE: DNA
<213> ORGANISM: Homo sapiens

<400> SEQUENCE: 4
cccgtacttc gctaacttta aacg                                   24

<210> SEQ ID NO 5
<211> LENGTH: 19
<212> TYPE: DNA
<213> ORGANISM: Homo sapiens

<400> SEQUENCE: 5
taggaaacgg gtttcgacg                                         19

<210> SEQ ID NO 6
<211> LENGTH: 19
<212> TYPE: DNA
<213> ORGANISM: Homo sapiens

<400> SEQUENCE: 6
ccgtccactt tctttaccg                                         19

<210> SEQ ID NO 7
<211> LENGTH: 20
<212> TYPE: DNA
<213> ORGANISM: Homo sapiens

<400> SEQUENCE: 7
atttttgcgg tcgtagcggt                                        20

<210> SEQ ID NO 8
<211> LENGTH: 21
<212> TYPE: DNA
<213> ORGANISM: Homo sapiens

<400> SEQUENCE: 8
ttctacgaca aatctaacga a                                      21

<210> SEQ ID NO 9
<211> LENGTH: 30
<212> TYPE: DNA
<213> ORGANISM: Artificial Sequence
<220> FEATURE:
<223> OTHER INFORMATION: synthetic

<400> SEQUENCE: 9
accaccaccc aacacacaat aacaaacaca                             30
```

```
<210> SEQ ID NO 10
<211> LENGTH: 24
<212> TYPE: DNA
<213> ORGANISM: Artificial Sequence
<220> FEATURE:
<223> OTHER INFORMATION: synthetic

<400> SEQUENCE: 10
acaaacgcga accgaacgaa acca                                          24

<210> SEQ ID NO 11
<211> LENGTH: 25
<212> TYPE: DNA
<213> ORGANISM: Artificial Sequence
<220> FEATURE:
<223> OTHER INFORMATION: synthetic

<400> SEQUENCE: 11
cgttaaacaa cgaaatccaa ccgaa                                         25

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
atatccaaaa cgccgcgaaa ctcc                                          24
```